United States Patent [19]
Fuss et al.

[11] Patent Number: 5,847,149
[45] Date of Patent: Dec. 8, 1998

[54] THIADIAZOLE DERIVATIVES, PROCESS FOR THEIR PREPARATION, AND THEIR USE AS PRECURSORS FOR THE PRODUCTION OF LIQUID CRYSTALS

[75] Inventors: Robert Walter Fuss, Kelkheim; Javier Manero, Frankfurt; Hubert Schlosser, Glashütten; Rainer Wingen, Hattersheim, all of Germany

[73] Assignee: Hoechst Aktiengesellschaft, Frankfurt, Germany

[21] Appl. No.: 680,898

[22] Filed: Jul. 16, 1996

Related U.S. Application Data

[63] Continuation of Ser. No. 377,850, Jan. 25, 1995, abandoned.

[30] Foreign Application Priority Data

Jan. 27, 1994 [DE] Germany .......................... 44 02 361.8

[51] Int. Cl.$^6$ ...................... C07D 285/12; C07D 401/04; C07D 239/34
[52] U.S. Cl. .......................... 548/136; 544/298; 544/315; 544/318; 546/268.7; 548/139
[58] Field of Search ..................................... 548/136, 139; 544/298, 315, 318; 546/268.7

[56] References Cited

U.S. PATENT DOCUMENTS

| | | | |
|---|---|---|---|
| 3,959,301 | 5/1976 | Dahle | 548/136 |
| 4,454,147 | 6/1984 | DiMenna et al. | 548/136 |
| 4,952,699 | 8/1990 | Yong et al. | 548/136 |
| 5,034,151 | 7/1991 | Shinjo et al. | 252/299.61 |
| 5,076,961 | 12/1991 | Nakamura et al. | 252/299.61 |
| 5,209,866 | 5/1993 | Reiffenrath et al. | 252/299.61 |
| 5,232,624 | 8/1993 | Reiffenrath et al. | 252/299.61 |

FOREIGN PATENT DOCUMENTS

| | | |
|---|---|---|
| PA 0 332 024 | 2/1989 | European Pat. Off. . |
| PA 0 332 025 | 2/1989 | European Pat. Off. . |
| PA 0 335 348 A2 | 3/1989 | European Pat. Off. . |
| 38 19 972 | 1/1989 | Germany . |
| 40 21 811 | 1/1991 | Germany . |
| 50/92279 | 7/1975 | Japan . |
| WO 88/08019 | 10/1988 | WIPO . |

*Primary Examiner*—Yogendra N. Gupta
*Attorney, Agent, or Firm*—Frommer Lawrence & Haug LLP

[57] ABSTRACT

Thiadiazole derivatives of the formula (I)

$$X\text{-}B\text{-}A^1\text{-}(M^1\text{-}A^2\text{-})_m(M^2\text{-}A^3)_n\text{-}R^1 \quad (I)$$

in which the symbols and indices have the following meanings:

X is Cl, Br or I;

B is 1,3,4-thiadiazole-2,5-diyl;

$A^1$, $A^2$ and $A^3$ are identical or different and are substituted or unsubstituted 1,4-phenylene, pyrazine-2,5-diyl, pyridazine-3,6-diyl, pyridine-2,5-diyl, pyrimidine-2,5-diyl, trans-1,4-cyclohexylene, 1,3,4-thiadiazole-2,5-diyl, 1,3-dioxane-2,5-diyl, 1,3-dithiane-2,5-diyl, 1,3-thiazole-2,4-diyl, 1,3-thiazole-2,5-diyl, thiophene-2,4-diyl, thiophene-2,5-diyl, piperazine-1,4-diyl, piperazine-2,5-diyl, naphthalene-2,6-diyl, bicyclo[2.2.2]octane-1,4-diyl, or 1,3-dioxaborinane-2,5-diyl;

$M^1$ and $M^2$ are identical or different and are —CO—O—, —O—CO—, —O—CO—O—, —O—CS—O—, —CH$_2$—O—, —O—CH$_2$—, —CH=CH—, —C≡C— or a single bond;

$R^1$ is —O-benzyl, H, an alkyl group having 1 to 12 carbon atoms or an alkoxy group having 1 to 12 carbon atoms;

m and n are 0 or 1.

The novel compounds allow the synthesis of a wide range of 1,3,4-thiadiazole derivatives, as employed, for example, as components of liquid-crystal mixtures, in a significantly reduced number of synthesis steps.

10 Claims, No Drawings

THIADIAZOLE DERIVATIVES, PROCESS FOR THEIR PREPARATION, AND THEIR USE AS PRECURSORS FOR THE PRODUCTION OF LIQUID CRYSTALS

This application is a continuation of application Ser. No. 08/377,850, filed Jan. 25, 1995, abandoned.

The unusual combination of anisotropic and fluid behavior of liquid crystals has led to their use in electro-optical switching and display devices, where their electrical, magnetic, elastic and/or thermal properties can be utilized for changes in alignment. Optical effects can be achieved, for example, with the aid of birefringence, the inclusion of dichroitically absorbing dyes ("guest-host mode") or light scattering.

In addition to nematic and cholesteric liquid crystals, optically active smectic liquid-crystal phases have been increasing in importance in recent years.

In order to satisfy the constantly rising practical requirements in the various areas of application, there is a continual demand for novel improved liquid-crystal mixtures and thus also for a large number of mesogenic compounds of various structures.

The preparation processes for components of such liquid-crystal mixtures also have to meet constantly rising requirements, in particular with respect to the ecological effects, but also with respect to the process economy.

It is known that 2,5-disubstituted 1,3,4-thiadiazoles are highly suitable as chiral and achiral components of liquid-crystal mixtures. Such compounds are described, for example, in EP-A-0 335 348, WO-A 88/08019, DE-A-40 21 811, DE-A-38 19 972, JP-A 50/92 279, EP-A-0 332 024 and EP-A 0 332 025.

The preparation of liquid-crystalline 2,5-disubstituted 1,3,4-thiadiazoles in accordance with the prior art, as described, for example, in DE-A-38 19 972, comprises reacting a substituted aromatic carboxylic acid hydrazide with a substituted aromatic carboxylic acid chloride to give the corresponding 1,2-diacylhydrazine. In the next step, ring closure to give the 1,3,4-thiadiazole is completed with the aid of diphosphorus pentasulfide or 2,4-bis(4-methoxyphenyl)-1,3-dithia-2,4-diphophetane 2,4-disulfide (Lawesson's reagent) in basic medium. The resultant products are sometimes contaminated with the corresponding 2,5-disubstituted 1,3,4-oxadiazoles.

The disadvantages of the process described are the requisite handling of the carcinogenic hydrazine and the liberation of hydrogen sulfide during the reaction with Lawesson's reagent. Furthermore, for every desired final compound, a corresponding carboxylic acid hydrazide must be prepared, then reacted with the suitable acid chloride to give the requisite 1,2-diacylhydrazine compound and then derivatized to give the 1,3,4-thiadiazole.

The disadvantages described are overcome by the novel compounds of the formula (I)

$$X\text{-}B\text{-}A^1\text{-}(M^1\text{-}A^2\text{-})_m(M^2\text{-}A^3)_n\text{-}R^1 \qquad (I)$$

in which the symbols and indices have the following meanings:

X is Cl, Br or I;
B is 1,3,4-thiadiazole-2,5-diyl;
$A^1$, $A^2$ and $A^3$ are identical or different and are 1,4-phenylene, in which one or more H atoms may be replaced by F, Cl and/or CN, pyrazine-2,5-diyl, in which one or two H atoms may be replaced by F, Cl and/or CN, pyridazine-3,6-diyl, in which one or two H atoms may be replaced by F, Cl and/or CN, pyridine-2,5-diyl, in which one or more H atoms may be replaced by by F, Cl and/or CN, pyrimidine-2,5-diyl, in which one or two H atoms may be replaced by F, Cl and/or CN, trans-1,4-cyclohexylene, in which one or two H atoms may be replaced by CN and/or $CH_3$, 1,3,4-thiadiazole-2,5-diyl, 1,3-dioxane-2,5-diyl, 1,3-dithiane-2,5-diyl, 1,3-thiazole-2,4-diyl, in which one H atom may be replaced by F, Cl and/or CN, 1,3-thiazole-2,5-diyl, in which one H atom may be replaced by F, Cl and/or CN, thiophene-2,4-diyl, in which one H atom may be replaced by F, Cl and/or CN, thiophene-2,5-diyl, in which one or two H atoms may be replaced by F, Cl and/or CN, piperazine-1,4-diyl, piperazine-2,5-diyl, naphthalene-2,6-diyl, in which one or more H atoms may be replaced by F, Cl and/or CN, bicyclo[2.2.2]octane-1,4-diyl, in which one or more H atoms may be replaced by F, Cl and/or CN, or 1,3-dioxaborinane-2,5-diyl;
$M^1$ and $M^2$ are identical or different and are —CO—O—, —O—CO—, —O—CO—O—, —O—CS—O—, —$CH_2$—O—, —O—$CH_2$—, —CH=CH—, —C≡C— or a single bond;
$R^1$ is —O-benzyl, H, an alkyl group having 1 to 12 carbon atoms or an alkoxy group having 1 to 12 carbon atoms;
m and n are 0 or 1.

Preference is given to compounds of the formula (I) in which the symbols and indices have the following meanings:
X is Br or I;
$A^1$, $A^2$ and $A^3$ are identical or different and are 1,4-phenylene, in which one or more H atoms may be replaced by F, pyridine-2,5-diyl, in which one or more H atoms may be replaced by F, pyrimidine-2,5-diyl, in which one or two H atoms may be replaced by F, trans-1,4-cyclohexylene, or naphthalene-2,6-diyl, in which one or more H atoms may be replaced by F;
$M^1$ and $M^2$ are —$CH_2$—O—, —O—$CH_2$— or a single bond.

Particular preference is given to compounds of the formula (I) in which the symbols and indices have the following meanings:
X is Br;
$A^1$, $A^2$ and $A^3$ are identical or different and are 1,4-phenylene, in which one or more H atoms may be replaced by F, pyridine-2,5-diyl, in which one or more H atoms may be replaced by F, pyrimidine-2,5-diyl, in which one or two H atoms may be replaced by F, trans-1,4-cyclohexylene, or naphthalene-2,6-diyl, in which one or more H atoms may be replaced by F;
$M^1$ and $M^2$ are —$CH_2$—O—, —O—$CH_2$— or a single bond.

Very particular preference is given to compounds of the formula (I) in which the symbols and indices have the following meanings:
X is Br;
$A^1$, $A^2$ and $A^3$ are identical or different and are 1,4-phenylene, in which one or two H atoms may be replaced by fluorine, pyridine-2,5-diyl, in which one or two H atoms may be replaced by F, pyrimidine-2,5-diyl, naphthalene-2,6-diyl or trans-1,4-cyclo-hexylene;
$M^1$ and $M^2$ are —O—$CH_2$— or a single bond.

Most preference is given to compounds of the formula (I) in which the symbols and indices have the following meanings:
X is Br;
$A^1$, $A^2$ and $A^3$ are 1,4-phenylene, pyridine-2,5-diyl, in which one H atom may also be replaced by F, or trans-1,4-cyclohexylene;
$M^1$ and $M^2$ are —O—$CH_2$— or a single bond.

Of these, the following structures of the formula (I) in particular are preferred:

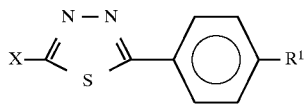 (Ia)

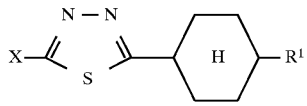 (Ib)

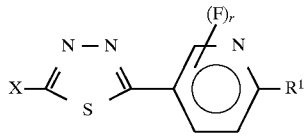 (Ic)

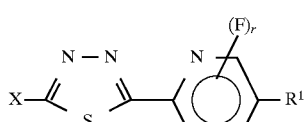 (Id)

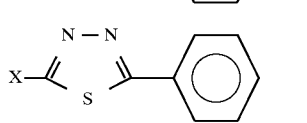 (Ie)

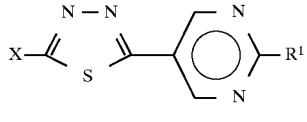 (If)

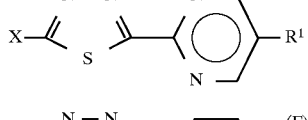 (Ig)

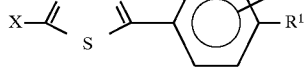 (Ih)

where $R^1$ and X are as defined under the formula (I), and r is 0, 1 or 2.

The novel compounds allow the synthesis of a wide range of 1,3,4-thiadiazole derivatives, as employed, for example, as components of liquid-crystal mixtures, in a significantly reduced number of synthesis steps.

For example, the novel compounds can be prepared starting from commercially available 2-amino-1,3,4-thiadiazole, which is reacted with bromine (in excess) in hydrobromic acid, and the resultant 2-amino-5-bromo-1,3,4-thiadiazole can be diazotized in situ at a suitable temperature using sodium nitrite. Interim isolation of the 2-amino-5-bromo-1,3,4-thiadiazole and performance of the diazotization in phosphoric acid analogously to DE 24 32 005 is unnecessary, just as the reaction on the copper sulfate/sodium bromide catalyst (Sandmeyer reaction) can be omitted.

2,5-Dibromo-1,3,4-thiadiazole can now be reacted further with an organometallic compound of the formula (II)

$$Y-A^1(-M^1-A^2)_m(-M^2-A^3)_n-R^1 \quad (II)$$

in which the symbols and indices are as defined under the formula (I), and
Y is halogen—Mg—, Li— or -BQ$^1$Q$^2$, in which $Q_1$ and $Q_2$ are identical or different and are —OH, $C_1$—$C_4$-alkoxy, $C_1$–$C_4$-alkyl, phenyl, which may be substituted by $C_1$–$C_4$-alkyl, $C_1$–$C_4$-alkoxy or halogen, or halogen or $Q_1$ and $Q_2$ together form a $C_1$–$C_4$-alkylenedioxy group, a methylene group, which may be substituted by one or two $C_1$–$C_4$-alkyl groups, or $Q_1$ and $Q_2$ and the boron atom together are part of a boroxine ring:

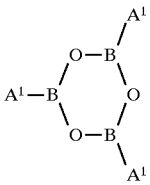

Y is preferably a boronic acid radical —B(OH)$_2$. The corresponding compound of the formula (II) can be reacted with 2,5-dibromo-1,3,4-thiadiazole with transition-metal catalysis. In order to carry out the process, the aromatic boronic acid, the aromatic halogen compound or the perfluoroalkyl sulfonate, the base, the catalytic amount of metallic, supported or unsupported palladium and the catalytic amount of a ligand are preferably introduced into an inert solvent or an inert solvents mixture and stirred at a temperature of –78° C. to 200° C., preferably at from 30° C. to 170° C., particularly preferably at from 50° C. to 150° C., especially preferably at from 60° to 120° C., for a period of from 1 hour to 100 hours, preferably for from 5 hours to 70 hours, particularly preferably for from 10 hours to 50 hours, especially preferably for from 15 hours to 30 hours. When the reaction is complete, the Pd catalyst produced as a solid is removed by filtration, and the crude product is freed from the solvent or solvents and subsequently purified by methods known to a person skilled in the art and appropriate to the particular product, for example by recrystallization, distillation, sublimation, zone melting, melt crystallization or chromatography.

Examples of solvents which are suitable for this process are ethers, for example diethyl ether, dimethoxymethane, diethylene glycol dimethyl ether, tetrahydrofuran, dioxane, diisopropyl ether, tert-butyl methyl ether, hydrocarbons, for example hexane, isohexane, heptane, cyclohexane, benzene, toluene and xylene, alcohols, for example methanol, ethanol, 1-propanol, 2-propanol, ethylene glycol, 1-butanol, 2-butanol and tert-butanol, ketones, for example acetone, ethyl methyl ketone and isobutyl methyl ketone, amides, for example dimethylformamide, dimethylacetamide and N-methylpyrrolidone, nitriles, for example acetonitrile, propionitrile and butyronitrile, water and mixtures thereof.

Preferred solvents are ethers, such as dimethoxyethane, diethylene glycol dimethyl ether, tetrahydrofuran, dioxane and diisopropyl ether, hydrocarbons, such as hexane, heptane, cyclohexane, benzene, toluene and xylene, alcohols, such as methanol, ethanol, 1-propanol, 2-propanol, 1-butanol, 2-butanol and ethylene glycol, ketones, such as ethyl methyl ketone and isobutyl methyl ketone, amides, such as dimethylformamide, dimethylacetamide, N-methylpyrrolidone and hexamethylphosphoric triamide, water and mixtures thereof.

Particularly preferred solvents are ether, for example dimethoxyethane, tetrahydrofuran, hydrocarbons, for example cyclohexane, benzene, toluene and xylene, alcohols, for example ethanol, 1-propanol and 2-propanol, water and mixtures thereof.

Most preference is given to dimethoxyethane, benzene, toluene, ethanol, water and mixtures thereof.

Bases which are preferred in the process are alkali metal and alkaline earth metal hydroxides, alkali metal and alkaline earth metal carbonates, alkali metal hydrogencarbonates, alkali metal and alkaline earth metal acetates, alkali metal and alkaline earth metal alkoxides, and primary, secondary and tertiary amines.

Particular preference is given to alkali metal and alkaline earth metal hydroxides, alkali metal and alkaline earth metal carbonates and alkali metal hydrogencarbonates.

Most preference is given to alkali metal hydroxides, alkali metal carbonates and alkali metal hydrogencarbonates, such as lithium carbonate, sodium carbonate and potassium carbonate.

The base is preferably employed in the process in a proportion of from 100 to 1000 mol %, particularly preferably from 100 to 500 mol %, very particularly preferably from 150 to 400 mol %, especially from 180 to 250 mol %, based on the aromatic boronic acid.

The catalyst used is metallic palladium, preferably palladium in powdered form or on a support material, for example palladium on activated charcoal, palladium on aluminum oxide, palladium on barium carbonate, palladium on barium sulfate, palladium on aluminum silicates, such as montmorillonite, palladium on $SiO_2$ and palladium on calcium carbonate, in each case having a palladium content of from 0.5 to 10% by weight, particularly preferably palladium in powdered form, and palladium on activated charcoal, palladium on barium carbonate or calcium carbonate, and palladium on barium sulfate, in each case having a palladium content from 0.5 to 10% by weight, especially palladium on activated charcoal having a palladium content of 10% by weight.

It is also possible to employ catalysts containing other dopes, for example lead (Lindlar catalyst), in addition to palladium and the support material.

The metallic palladium catalyst is employed in the process in a proportion of from 0.1 to 10 mol %, preferably from 0.2 to 5 mol %, particularly preferably from 0.5 to 3 mol %, especially preferably from 0.5 to 1.5 mol %, based on the aromatic halogen compound.

Examples of ligands which are suitable for the process are phosphines, such as trialkylphosphines, tricycloalkylphosphines and triarylphosphines, where the three substituents on the phosphorus may be identical or different, chiral or achiral and where one or more of the ligands can link the phosphorus groups of more than one phosphine and where some of these links can also be one or more metal atoms.

Examples of phosphines which can be used for the purposes of the novel process are trimethylphosphine, tributylphosphine, tricyclohexylphosphine, triphenylphosphine, tritolylphosphine, tris(4-dimethylaminophenyl)phosphine, bis(diphenylphosphino)methane, 1,2-bis(diphenylphosphino)ethane, 1,3-bis(diphenylphosphino)propane and 1,1'-bis(diphenylphosphineo)ferrocene.

Other suitable ligands are, for example, diketones, for example acetylacetone and octafluoroacetylacetone, and tertiary amines, for example trimethylamine, triethylamine, tri-n-propylamine and triisopropylamine.

Preferred ligands are phosphines and diketones; phosphines are particularly preferred.

Very particularly preferred ligands are triphenylphosphine, 1,2-bis(diphenylphosphino)ethane, 1,3-bis(diphenylphosphino)propane and 1,1'-bis(diphenylphosphino)ferrocene, in particular triphenylphosphine.

The ligand is employed in the process in a proportion of from 0.1 to 20 mol %, preferably from 0.2 to 15 mol %, particularly preferably from 0.5 to 10 mol %, especially preferably from 1 to 6 mol %, based on the aromatic halogen compound or the perfluoroalkyl sulfonate. It is also possible, if desired, to employ mixtures of two or more different ligands.

Surprisingly, it is possible, through a simple choice of the stoichiometric ratios, selectively to prepare the novel mono-coupling product of the formula (I).

Transition metal-catalyzed coupling reactions of halogen compounds with boronic acids are described, for example, in DE-A-39 30 663, EP-A-0 354 434 and German Patent Application P 42 36 103.6 with the title "Process for the cross-coupling of aromatic boronic acids with aromatic halogen compounds or perfluoroalkyl sulfonates". In the process proposed therein, the boronic acid is coupled with aromatic halogen compounds or perfluoroalkyl sulfonates in the presence of a base and catalytic amounts of metallic palladium, either unsupported or on a support material, where a base and catalytic amounts of a ligand are added to the reaction mixture.

The boronic acids of the formula (II) can be prepared, for example, from the corresponding halides by reaction with magnesium to give the Grignard compound, reaction with an excess of, for example, methyl borate and subsequently acid hydrolysis. For the preparation of the various monocyclic, dicyclic and tricyclic systems, reference is made, for example, to DE-A 23 44 732, 24 50 088, 24 29 093, 25 02 904, 26 36 684, 27 01 591 and 27 52 975 for compounds containing 1,4-cyclohexylene and 1,4-phenylene groups; DE-A 26 41 724 for compounds containing pyrimidine-2,5-diyl groups; DE-A 40 26 223 and EP-A 03 91 203 for compounds containing pyridine-2,5-diyl groups; DE-A 32 31 462 for compounds containing pyridazine-3,6-diyl groups; N. Miyaura, T. Yanagi and A. Suzuki in Synthetic Communications 11 (1981), pp. 513–519, DE-C-3 930 663, M. J. Sharp, W. Cheng, V. Snieckus in Tetrahedron Letters 28 (1987), pp. 5093 ff.; G. W. Gray in J. Chem. Soc. Perkin Trans II, 1989, pp. 2041 ff., and Mol. Cryst. Liq. Cryst. 172 (1989), pp. 165 ff., 204 (1991), pp. 43 ff. and pp. 91 ff.; EP-A 0 449 015; WO 89/12039; WO 89/03821; EP-A 0 354 434 for the direct linking of aromatics and heteroaromatics; DE-A 32 01 721 for compounds containing —$CH_2CH_2$—bridges, and Koji Seto et al. in Liquid Crystals 8 (1990), pp. 861–870, for compounds containing —C≡C— bridges.

The preparation of disubstituted pyridines, disubstituted pyrazines, disubstituted pyrimidines and disubstituted pyridazines is given, for example, in the corresponding volumes of the series "The Chemistry of Heterocyclic Compounds" by A. Weissberger and E. C. Taylor (editors).

2,5-Dibromo-1,3,4-thiadiazole can be coupled, in particular, with the following boronic acids to give compounds of the formula (I):

4-alkylphenylboronic acids
4-alkoxyphenylboronic acids
2-alkylpyridine-5-boronic acids
2-alkoxypyridine-5-boronic acids
2-alkyl-6-fluoropyridine-5-boronic acids
2-alkyl-3-fluoropyridine-5-boronic acids
2-alkoxy-6-fluoropyridine-5-boronic acids
2-alkoxy-3-fluoropyridine-5-boronic acids
5-alkyl-6-fluoropyridine-2-boronic acids
5-alkyl-3-fluoropyridine-2-boronic acids
5-alkoxy-6-fluoropyridine-2-boronic acids
5-alkoxy-3-fluoropyridine-2-boronic acids
3-alkylpyridazine-6-boronic acids
3-alkoxypyridazine-6-boronic acids
2-alkylpyrazine-5-boronic acids 2-alkoxypyrazine-5-boronic acids
2-alkylnaphthyl-6-boronic acids
2-alkoxynaphthyl-6-boronic acids
2-(4-alkylphenyl)pyridine-5-boronic acids
2-(4-alkoxyphenyl)pyridine-5-boronic acids
3-(4-alkylphenyl)pyridine-6-boronic acids
3-(4-alkoxyphenyl)pyridine-6-boronic acids
3-(4-alkylphenyl)pyrazine-5-boronic acids
3-(4-alkoxyphenyl)pyrazine-5-boronic acids
3-(4-alkylphenyl)pyridazine-6-boronic acids
3-(4-alkoxyphenyl)pyridazine-6-boronic acids
5-(3-alkylpyridin-2-yl)pyrimidine-2-boronic acids
5-(3-alkoxypyridin-2-yl)pyrimidine-2-boronic acids
2-(3-alkylpyridin-2-yl)pyrimidine-5-boronic acids
2-(3-alkoxypyridin-2-yl)pyrimidine-5-boronic acids
3-(3-alkylpyridin-2-yl)pyrazine-5-boronic acids
3-(3-alkoxypyridin-2-yl)pyrazine-5-boronic acids
3-(3-alkylpyridin-2-yl)pyridazine-6-boronic acids
3-(3-alkoxypyridin-2-yl)pyridazine-6-boronic acids
5-(2-alkylpyridin-5-yl)pyrimidine-2-boronic acids
5-(2-alkoxypyridin-5-yl)pyrimidine-2-boronic acids
2-(2-alkylpyridin-5-yl)pyrimidine-5-boronic acids
2-(2-alkoxypyridin-5-yl)pyrimidine-5-boronic acids
3-(2-alkylpyridin-5-yl)pyrazine-5-boronic acids
3-(2-alkoxypyridin-5-yl)pyrazine-5-boronic acids
3-(2-alkylpyridin-5-yl)pyridazine-6-boronic acids
3-(2-alkoxypyridin-5-yl)pyridazine-6-boronic acids
5-(2-fluoro-3-alkylpyridin-6-yl)pyrimidine-2-boronic acids
5-(2-fluoro-3-alkoxypyridin-6-yl)pyrimidine-2-boronic acids
2-(2-fluoro-3-alkylpyridin-6-yl)pyrimidine-5-boronic acids
2-(2-fluoro-3-alkoxypyridin-6-yl)pyrimidine-5-boronic acids
3-(2-fluoro-3-alkylpyridin-6-yl)pyrazine-5-boronic acids
3-(2-fluoro-3-alkoxypyridin-6-yl)pyrazine-5-boronic acids
3-(2-f luoro-3-alkylpyridin-6-yl)pyridazine-6-boronic acids
3-(2-fluoro-3-alkoxypyridin-6-yl)pyridazine-6-boronic acids
5-(2-alkyl-6-f luoropyridin-5-yl)pyrimidine-2-boronic acids
5-(2-alkoxy-6-fluoropyridin-5-yl)pyrimidine-2-boronic acids
2-(2-alkyl-6-fluoropyridin-5-yl)pyrimidine-5-boronic acids
2-(2-alkoxy-6-fluoropyridin-5-yl)pyrimidine-5-boronic acids
3-(2-alkyl-6-fluoropyridin-5-yl)pyrazine-5-boronic acids
3-(2-alkoxy-6-fluoropyridin-5-yl)pyrazine-5-boronic acids
3-(2-alkyl-6-fluoropyridin-5-yl)pyridazine-6-boronic acids
3-(2-alkoxy-6-fluoropyridin-5-yl)pyridazine-6-boronic acids The invention therefore also relates to a process for the preparation of 2-halo-1,3,4-thiadiazole derivatives of the formula (I)

$$X\text{-}B\text{-}A^1\text{-}(M^1\text{-}A^2\text{-})_m(M^2\text{-}A^3)_n\text{-}R^1 \qquad (I)$$

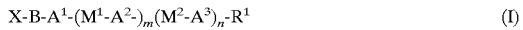

in which the symbols and indices are as defined above, which comprises
a) reacting 2-amino-1,3,4-thiadiazole with bromine,
b) diazotizing the resultant 2-bromo-1,3,4-thiadiazole using sodium nitrite,
c) reacting the resultant diazonium salt with bromine, and
d) reacting the resultant 2,5-dibromo-1,3,4-thiadiazole with a boron compound of the formula (II)

$$Q^1Q^2\text{-}B\text{-}A^1\text{-}(M^1\text{-}A^2)_m(\text{-}M^2\text{-}A^3)_n\text{-}R^1 \qquad (II)$$

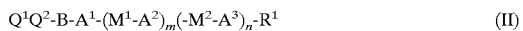

in which the symbols and indices are as defined above, and $Q_1$ and $Q_2$ are identical or different and are —OH, $C_1$–$C_4$-alkoxy, $C_1$–$C_4$-alkyl, phenyl, which may be substituted by $C_1$–$C_4$-alkyl, $C_1$–$C_4$-alkoxy or halogen, or halogen or $Q_1$ and $Q_2$ together form a $C_1$–$C_4$-alkylenedioxy group, a methylene group, which may be substituted by one or two $C_1$–$C_4$-alkyl groups, or $Q_1$ and $Q_2$ and the boron atom together are part of a boroxine ring:

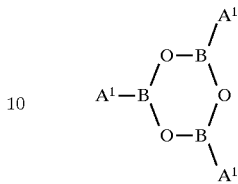

with transition-metal catalysis in an inert solvent at a temperature of from −78° C. to 200° C.

The novel compounds of the formula (I) are versatile synthesis units for the preparation of polycyclic 1,3,4-thiadiazole derivatives which can be employed in many areas of organic chemistry, for example for the preparation of components for liquid-crystal mixtures, pharmaceuticals, cosmetics or crop-protection agents.

They are preferably used as intermediates for the preparation of components for liquid-crystal mixtures, in particular for ferroelectric mixtures. Such components are described, for example, in EP-A-0 541 081, EP-A-0 335 348, WO-A 88/08019, DE-A-40 21 811, DE-A-38 19 972, JP-A-50/92279, EP-A-0 332 024 and EP-A-0 332 025.

The novel compounds of the formula (I) can be derivatized successively and selectively via one or two different functionalities, the halogen and, if appropriate, the benzyl ether function.

Thus, they can be reacted with boronic acids of the formula (III)

$$R^2\text{-}A^4\text{-}B(OH)_2 \qquad (III)$$

in which
$R^2$ is H, alkyl having 1 to 18 carbon atoms, in which one or more non-adjacent —CH$_2$-groups may also be replaced by —O—, —C(O)—, —CH=CH—, —OC(O)— or —Si(CH$_3$)$_2$—, and $A^4$ is 1,4-phenylene, in which one or more H atoms may be replaced by F, Cl and/or CN, pyrazine-2,5-diyl, in which one or two H atoms may be replaced by F, Cl and/or CN, pyridazine-3,6-diyl, in which one or two H atoms may be replaced by F, Cl and/or CN, pyridine-2,5-diyl, in which one or more H atoms may be replaced by F, Cl and/or CN, pyrimidine-2,5-diyl, in which one or two H atoms may be replaced by F, Cl and/or CN, trans-1,4-cyclohexylene, in which one or two H atoms may be replaced by CN and/or CH$_3$, 1,3,4-thiadiazole-2,5-diyl, 1,3-dioxane-2,5-diyl, 1,3-dithiane-2,5-diyl, 1,3-thiazole-2,4-diyl, in which one H atom may be replaced by F, Cl and/or CN, 1,3-thiazole-2,5-diyl, in which one H atom may be replaced by F, Cl and/or CN, thiophene-2,4-diyl, in which one H atom may be replaced by F, Cl and/or CN, thiophene-2,5-diyl, in which one or two H atoms may be replaced by F, Cl and/or CN, piperazine-1,4-diyl, piperazine-2,5-diyl, naphthalene-2,6-diyl, in which one or more H atoms may be replaced by F, Cl and/or CN, bicyclo[2.2.2]octane-1,4-diyl, in which one or more H atoms may be replaced by F, Cl and/or CN, or 1,3-dioxaborinane-2,5-diyl, via the halogen function by metal-catalyzed processes, as described, for example, in DE-C 3 930 663 and EP-A 354 434, to give intermediates of the formula (IV)

$$R^2\text{-}A^4\text{—}B\text{—}A^1(\text{-}M^1\text{-}A^2)_m(\text{-}M^2\text{-}A^3)_n\text{-}R^1 \qquad (IV)$$

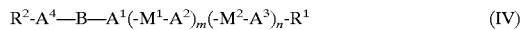

in which the symbols and indices are as defined under the formulae (I) and (III).

Preference is given to the reaction, for example to the compounds of the formula (IV), by a process proposed in German Patent Application P 42 36 103.6 with the title "Process for cross-coupling of aromatic boronic acids with aromatic halogen compounds or perfluoroalkyl sulfonates", in which the novel compound is coupled with aromatic halogen compounds or perfluoroalkyl sulfonates in the presence of a base and in the presence of catalytic amounts of metallic palladium, either unsupported or on a support material, which comprises adding a base and catalytic amounts of a ligand to the reaction mixture.

It is furthermore possible to react the novel compounds of the formula (I) with alkyl-organometallic compounds by metal-catalyzed processes, as described, for example in DE-A 3 930 663 and EP-A 354 434, to give intermediates of the formula (V)

$$R^3-B-A^1(-M^1-A^2)_m(-M^2-A^3)_n-R^1 \quad (V)$$

in which $R^3$ is alkyl having 1 to 18 carbon atoms, in which one or more non-adjacent —CH$_2$— groups may also be replaced by —O—, —CH=CH— or —Si(CH$_3$)$_2$—, where —O— must not be bonded directly to the ring, and the other symbols are as defined under the formula (I).

It is furthermore possible to convert the halogen function in the compounds of the formula (I) into an OH group by reaction with OH-nucleophiles, giving intermediates of the formula (VI)

$$HO-B-A^1(-M^1-A^2)_m(-M^2-A^3)_nR^1 \quad (VI)$$

in which the symbols and indices are as defined under the formula (I).

These intermediates (VI) can be converted into intermediates of the formula (VII)

$$R^4-O-B-A^1(-M^1-A^2)_m(-M^2-A^3)_n-R^1 \quad (VII)$$

in which $R^4$ is alkyl having 1 to 18 carbon atoms, in which one or more non-adjacent —CH$_2$— groups may also be replaced by —O—, —C(=O)—, —CH=CH— or —Si(CH$_3$)$_2$—, and the other symbols are as defined under the formula (V), by standard methods for the synthesis of alkyl aryl ethers or aryl alkanoates.

Furthermore, intermediates of the formula (VI) can be converted into intermediates of the formula (VIII)

$$R^2-A^4—COO-B-A^1(-M^1-A^2)_m(-M^2-A^3)_n-R^1 \quad (VIII)$$

in which the symbols and indices are as defined under the formula (III), by standard methods by reaction with carboxylic acids or carboxylic acid derivatives (for example halides or anhydrides).

In the case of compounds where $R^1$=—O-benzyl, intermediates containing a phenolic OH function can be produced by cleavage of the benzyl ether function in the intermediates (I), (IV), (V), (VII) and (VIII) by standard methods (for example described in T. W. Greene, P. G. M. Wuts, Protective Groups in Organic Synthesis, J. Wiley & Sons, New York, 1991, pp. 156–160):

$$X-B-A^1(-M^1-A^2)_m(-M^2-A^3)_n—OH \quad (IX) \text{ from (I)}$$

$$R^2-A^4-B-A^1(-M^1-A^2)_m(-M^2-A^3)_n—OH \quad (X) \text{ from (IV)}$$

$$R^3-B-A^1(-M^1-A^2)_m(-M^2-A^3)_n—OH \quad (XI) \text{ from (V)}$$

$$R^4—O-B-A^1(-M^1-A^2)_m(-M^2-A^3)_n—OH \quad (XII) \text{ from (VII)}$$

$$R^2-A^4—COO-B-A^1(-M^1-A^2)_m(-M^2-A^3)_n—OH \quad (XIII) \text{ from (VIII)}$$

The phenolic compounds of the formulae (IX) to (XIII) can be converted into numerous types of components for liquid-crystalline mixtures by standard methods. For example, reaction with alkyl halides or equivalent alkylating agents gives aryl alkyl ethers of the formula (XIV)

$$R^2-A^4-B-A^1(-M^1-A^2)_m(-M^2-A^3)_n—OR^4 \quad (XIV) \text{ from (X)}$$

in which the symbols are as defined under the formulae (III) and (IV).

Analogous reactions can be carried out with (XI), (XII) and (XIII).

Furthermore, reaction with carboxylic acids or carboxylic acid derivatives (for example halides or anhydrides) gives aryl carbonates, for example (XV) from (XI), $$R^3-B-A^1(-M^1-A^2)_m(-M^2-A^3)_n—OOC—A^4-R^2 \quad (XV)$$

in which the symbols are as defined under the formulae (X) and (VIII). Analogous reactions can be carried out with (X), (XII) and (XIII).

The novel compounds of the formula (I) are preferably used in one of the above-described ways for the preparation of components of liquid crystals of the formula (XVI)

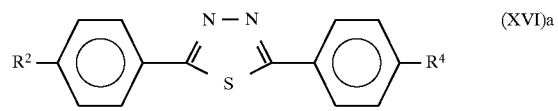
(XVI)a

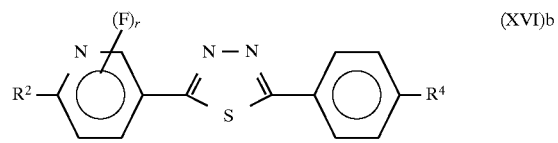
(XVI)b

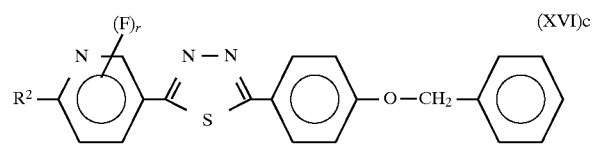
(XVI)c

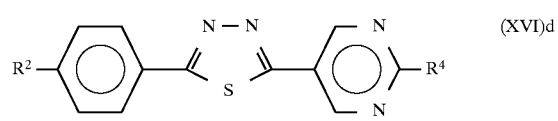
(XVI)d

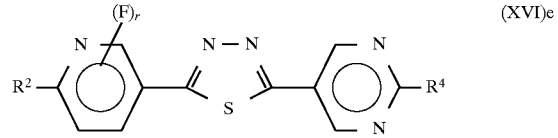
(XVI)e

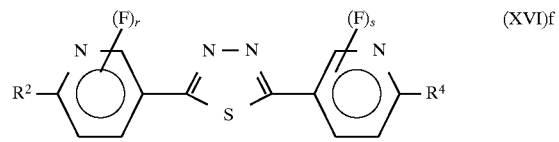
(XVI)f

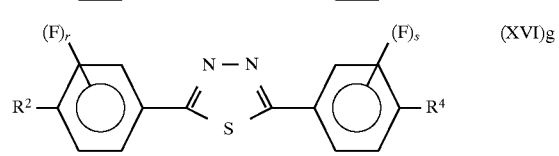
(XVI)g in which $R^2$ is as defined under the formula (III) and $R^4$ is as defined under the formula (VII), and r and s are identical or different and are 0, 1 or 2.

Use of the novel compounds of the formula (I) allows synthetic steps to be saved in the preparation of components for liquid-crystal mixtures, which brings enormous advantages, in particular in industrial-scale synthesis. The invention allows the production of a wide product range from a single intermediate in each case, greatly simplifying process control from a technical, economic and ecological point of view.

The invention is described in greater detail by means of the examples, but is not intended to be restricted thereto.

EXAMPLES

A. Synthesis of 2,5-dibromo-1,3,4-thiadiazole

Example 1

2,5-Dibromo-1,3,4-thiadiazole:

101.13 g (1.0 mol) of 2-amino-1,3,4-thiadiazole are introduced into an apparatus comprising a 2 l four-neck flask, precision glass stirrer, internal thermometer, 500 ml dropping funnel with pressure equalization and reflux condenser, and are dissolved in 1500.0 ml of hydrobromic acid (48%). The mixture is subsequently cooled to about −10C. 479.4 g (3.0 mol) of bromine are then added dropwise at such a rate that the internal temperature is kept at about −10° C. The mixture is stirred at this temperature for a further hour, and a solution of 165.6 g (2.4 mol) of sodium nitrite in 375.0 ml of water is added dropwise at such a rate that the internal temperature remains between −10° C. and −5° C. When the reaction is complete, the mixture is stirred for a further 1 hour at 0° C. and then a further 90–120 minutes at room temperature. The solution is then rendered alkaline by means of about 2400.0 ml of sodium hydroxide solution (32%) at a temperature below +15° C. For work-up, the mixture is extracted with 500.0 ml of diethyl ether for 1–3 hours in a continuous extraction apparatus (for solvents lighter than water), and the organic phase is subsequently dried with about 200.0 g of magnesium sulfate. The ether is removed in a rotary evaporator, and the residue is recrystallized from about 250 ml of ethanol, giving 134.4 g (0.55 mol) of 2,5-dibromo-1,3,4-thiadiazole.

B. Synthesis of compounds of the formula (I)

Example 1

2-Bromo-5-phenyl-1,3,4-thiadiazole

Phenylboronic acid (2.0 g, 16.4 mmol) and 2,5-dibromo-1,3,4-thiadiazole (4.0 g, 16.4 mmol) are refluxed for 24 hours in a mixture of sodium carbonate (15.64 g), toluene (60 ml), ethanol (30 ml) and water (30 ml) and tetrakis(triphenylphosphine)palladium(0) (10 mol %) as catalyst. Aqueous work-up and column chromatography ($SiO_2$, $CH_2Cl_2$/ethyl acetate 9:1) give 1.5 g (38% of theory) of 2-bromo-5-phenyl-1,3,4-thiadiazole.

$^1$H-NMR ($CDCl_3$/300 MHz): δ=7.51 ppm (m) 2H; 7.9 ppm (m) $^{13}$C-NMR ($CDCl_3$/75.4 MHz): δ=172.184 ppm S-C-phenyl, 138.001 ppm, 131.809 ppm, 129.396 ppm (2C), 129.302 ppm (C—Br), 127.876 ppm (2C).

Elemental analysis: $C_8H_5BrN_2S$, calc.: C 39.85%, H 2.075, N 11.62%, S 13.28%, Br 33.17%; found: C 40.04%, H 2.0%, N 11.75%, S 13.35%, Br 33.16%.

Example 2

2-Bromo-5-(4-octyloxyphenyl)-1,3,4-thiadiazole

4-Octyloxyphenylboronic acid (5.9 g, 23.6 mmol) and 2,5-dibromo-1,3,4-thiadiazole (5.8 g, 23.6 mmol) are refluxed for 14 hours in a mixture of sodium carbonate (19.56 g), toluene (70 ml), ethanol (35 ml) and water (35 ml) and tetrakis(triphenylphosphine)palladium(0) (10 mol %) as catalyst. Aqueous work-up and column chromatography ($SiO_2$, $CH_2Cl_2$) give 5.6 g (65% of theory) of 2-bromo-5-(4-octyloxyphenyl)-1,3,4-thiadiazole.

$^1$H-NMR ($CDCl_3$/300 MHz): δ=7.83 ppm (d) 2H; 7.0 ppm (d) 2H; 4.03 ppm (t) 2H; 1.77 ppm (m); 1.45 ppm (m); 1.31 ppm (m); 0.91 (m).

Example 3

2-Bromo-5-(4-pentylcyclohexylmethoxy)-1,3,4-thiadiazole

4-Pentylcyclohexylcarbinol (1.5 g, 8.15 mmol) are dissolved in dimethylformamide (40 ml), and sodium hydride (0.3 g, 12.23 mmol) is added at room temperature over a period of about 15 minutes. When the gas evolution is complete, 2-bromo-5-phenyl-1,3,4-thiadiazole (2.95 g, 12.23 mmol) is added to the resultant alkoxide, and the mixture is subsequently stirred at 50° C. for 6 hours, poured onto an ice/water mixture, filtered with suction and extracted. Separation by column chromatography ($SiO_2$, $CH_2Cl_2$) gives 1.2 g (43% of theory) of 2-bromo-5-(4-pentylcyclohexylmethoxy)-1,3,4-thiadiazole.

C. Use Examples

Use Example 1

2-(-6-Decyloxy-2-fluoropyrid-3-yl)-5-phenyl-1,3,4-thiadiazole (6-Decyloxy-2-fluoropyrid-3-yl)boronic acid (3.7 g, 12.4 mmol) and 2-bromo-5-phenyl-1,3,4-thiadiazole (1.0 g, 4.15 mmol) are refluxed for 6 hours in a mixture of sodium carbonate (3.95 g), toluene (50 ml), ethanol (25 ml) and water (25 ml) and tetrakis(triphenylphosphine)palladium(0) (5 mol %) as catalyst. Aqueous work-up and column chromatography ($SiO_2$, $CH_2Cl_2$) give 1.4 g (82% of theory) of 2-(6-decyloxy-2-fluoropyrid-3-yl)-5-phenyl-1,3,4-thiadiazole.

$^1$H-NMR ($CDCl_3$/300 MHz): δ=8.71 ppm (doublet of doublets) 1H; 8.03 ppm (doublet of doublets) 2H; 7.51 ppm (doublet of doublets) 3H; 6.79 ppm (doublet of doublets) 2H; 6.50 ppm (doublet) 1H; 4.35 ppm (triplet) 2H; 1.77 ppm (multiplet); 1.30 ppm (multiplet); 0.88 ppm (multiplet).

Use Example 2

2,5-Bis(6-dodecyloxy-2-fluoropyrid-3-yl)-1,3,4-thiadiazole (6-Dodecyloxy-2-fluoropyrid-3-yl)boronic acid (2.8 g, 8.6 mmol) and 2,5-dibromo-1,3,4-thiadiazole (1.0 g, 4.1 mmol) are refluxed for 15 hours in a mixture of sodium carbonate (3.91 g), toluene (40 ml), ethanol (20 ml) and water (20 ml) and tetrakis(triphenylphosphine)palladium(0) (5 mol %) as catalyst. Aqueous work-up and column chromatography ($SiO_2$, $CH_2Cl_2$) give 1.12 g (42% of theory) of 2,5-bis(4-dodecyloxy-2-fluoropyridyl)-1,3,4-thiadiazole.

$^1$H-NMR ($CDCl_3$/100 MHz): δ=8.7 ppm (doublet of doublets); 6.79 ppm (doublet of doublets); 4.33 ppm (triplet); 1.83 ppm (multiplet); 1.20 ppm (multiplet); 0.85 ppm (multiplet).

$^{19}$F-NMR ($CDCl_3$/94.2 MHz): δ=−67.1 ppm (doublet).

Use Example 3

(5-Phenyl-1,3,4-thiadiazol-2-yl)boronic acid

2-Bromo-5-phenyl-1,3,4-thiadiazole (1.7 g, 7.06 mmol) is dissolved in 10 ml of absolute tetrahydrofuran, and the solution is cooled to −78° C. under protective gas. 4.7 ml (7.5 mmol) of 1.6 molar n-butyllithium solution in n-hexane are added dropwise over the course of 30 minutes. The mixture is stirred at −78° C. for a further 30 minutes. 21.6 ml (21.6 mmol) of 1.0 molar ZnCl2 solution in diethyl ether are then slowly added dropwise, during which the temperature must not exceed −60° C. When the addition is complete, the mixture is stirred for a further 30 minutes. The corresponding boronic acids can be prepared analogously from 2-bromo-5-alkyl-1,3,4-thiadiazole or 2-bromo-5-alkoxy-1,3,4-thiadiazole. The crude (5-substituted 1,3,4-thiadiazol-2- yl)boronic acids are employed directly for the subsequent coupling reactions without isolation.

Use Example 4

2-(4-Cyclohexylphenyl)pyrimidin-2-yl)-5-ethyl-1,3,4-thiadiazole (5-Ethyl-1,3,4-thiadiazol-2-yl)boronic acid (1.0 g, 6.4 mmol) and 2-(4-cyclohexylphenyl)-5-bromopyrimidine (1.0 g, 3.2 mmol) are refluxed for 15 hours in a mixture of sodium carbonate (2.9 g), toluene (30 ml), ethanol (15 ml) and water (15 ml) and tetrakis(triphenylphosphine)palladium(0) (5 mol %) as catalyst. Aqueous work-up and column chromatography (SiO$_2$, CH$_2$Cl$_2$) give 0.65 g (58% of theory) of 2-(4-cyclohexylphenyl)pyrimidin-2-yl)-5-ethyl-1,3,4-thiadiazole.

Use Example 5

2-Octyl-5-phenyl-1,3,4-thiadiazole

2-Bromo-5-phenyl-1,3,4-thiadiazole (2.9 g, 12 mmol) is added to a 1-octylmagnesium bromide solution (4.6 g, 24 mmol) in THF (80 ml) under a protective-gas atmosphere, and 1,3-bis(diphenylphosphino)propylnickel(II) chloride (0.15 mmol), dissolved in . . . , is then added dropwise at −5° C. The mixture is subsequently stirred at this temperature for 4 hours. After acidification by means of hydrochloric acid (pH=2), the organic phase is separated off and evaporated. The crude product is recrystallized from acetonitrile.

Yield: 1.2 g (36% of theory) of 2-octyl-5-phenyl-1,3,4-thiadiazole.

We claim:

1. A 1,3,4-thiadiazole of the formula (I)

X-B-A$^1$-(M$^1$-A$^2$-)$_m$(M$^2$-A$^3$)$_n$-R$^1$   (I)

in which the symbols and indices have the following meanings:

X is Cl, Br or I;
B is 1,3,4-thiadiazole-2,5-diyl;
A$^1$, A$^2$ and A$^3$ are identical or different and are 1,4-phenylene, in which one or more H atoms may be replaced by F, Cl and/or CN, pyrazine-2,5-diyl, in which one or two H atoms may be replaced by F, Cl and/or CN, pyridazine-3,6-diyl, in which one or two H atoms may be replaced by F, Cl and/or CN, pyridine-2,5-diyl, in which one or more H atoms may be replaced by F, Cl and/or CN, pyrimidine-2,5-diyl, in which one or two H atoms may be replaced by F, Cl and/or CN, trans-1,4-cyclohexylene, in which one or two H atoms may be replaced by CN and/or CH$_3$, 1,3,4-thiadiazole-2,5-diyl, 1,3-dioxane-2,5-diyl, 1,3-dithiane-2,5-diyl, 1,3-thiazole-2,4-diyl, in which one H atom may be replaced by F, Cl and/or CN, 1,3-thiazole-2,5-diyl, in which one H atom may be replaced by F, Cl and/or CN, thiophene-2,4-diyl, in which one H atom may be replaced by F, Cl and/or CN, thiophene-2,5-diyl, in which one or two H atoms may be replaced by F, Cl and/or CN, piperazine-1,4-diyl, piperazine-2,5-diyl, naphthalene-2,6-diyl, in which one or more H atoms may be replaced by F, Cl and/or CN, bicyclo[2.2.2]-octane-1,4-diyl, in which one- or more H atoms may be replaced by F, Cl and/or CN, or 1,3-dioxaborinane-2,5-diyl;
M$^1$ and M$^2$ are identical or different and are —CO—O—, —O—CO—, —O—CO—O—, —O—CS—O—, —CH$_2$—O—, —O—CH$_2$—, —CH=CH—, —C≡C— or a single bond;
R$^1$ is —O-benzyl;
m and n are 0 or 1.

2. The 1,3,4-thiadiazole derivative of the formula (I) as claimed in claim 1, in which the symbols and indices have the following meanings:

X is Br or I;
A$^1$, A$^2$ and A$^3$ are identical or different and are 1,4-phenylene, in which one or more H atoms may be replaced by F, pyridine-2,5-diyl, in which one or more H atoms may be replaced by F, pyrimidine-2,5-diyl, in which one or two H atoms may be replaced by F, trans-1,4-cyclohexylene, or naphthalene-2,6-diyl, in which one or more H atoms may be replaced by F;
M$^1$ and M$^2$ are —CH$_2$—O—, —O—CH$_2$— or a single bond.

3. The 1,3,4-thiadiazole derivative of the formula (I) as claimed in claim 1, in which the symbols and indices have the following meanings:

X is Br;
A$^1$, A$^2$ and A$^3$ are identical or different and are 1,4-phenylene, in which one or more H atoms may be replaced by fluorine, pyridine-2,5-diyl, in which one or two H atoms may be replaced by F, pyrimidine-2,5-diyl, naphthalene-2,6-diyl, or trans-1,4-cyclohexylene;
M$^1$ and M$^2$ are —O—CH$_2$— or a single bond.

4. The 1,3,4-thiadiazole derivative of the formula (I) as claimed in claim 1, in which the symbols and indices have the-following meanings:

X is Br;
A$^1$, A$^2$ and A$^3$ are 1,4-phenylene, pyridine-2,5-diyl, in which one H atom may also be replaced by F, or trans-1,4-cyclohexylene;
M$^1$ and M$^2$ are —O—CH$_2$— or a single bond.

5. The thiadiazole derivative of the formula I as claimed in claim 1, having one of the structures Ia to Ih:

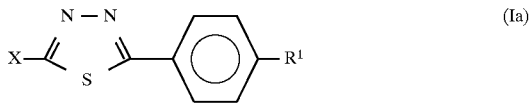
(Ia)

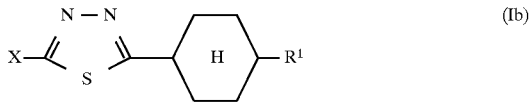
(Ib)

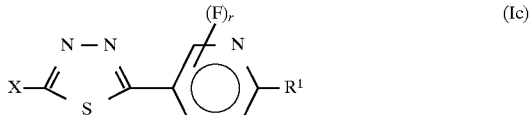
(Ic)

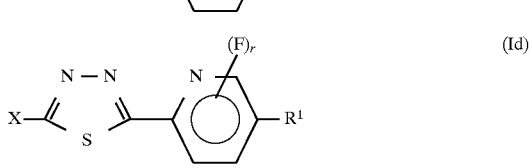
(Id)

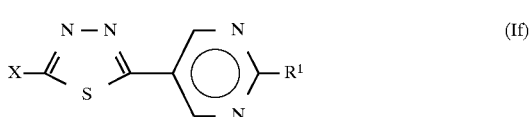
(If)

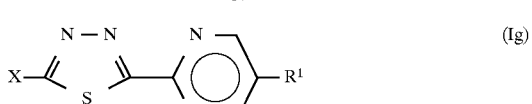
(Ig)

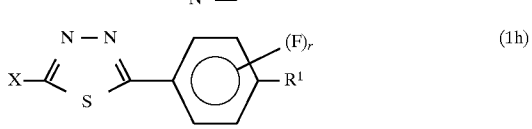
(Ih)

where X and R$^1$ are as defined under the formula (I) in claim 1, and r is 0, 1 or 2.

6. A 1,3,4-thiadiazole of formula (I)

$$X\text{-}B\text{-}A^1\text{-}(M^1\text{-}A^2\text{-})_m(M^2\text{-}A^3)_n R^1 \quad (I)$$

in which the symbols and indices have the following meanings:
X is Br or I;
B is 1,3,4-thiadiazole-2,5-diyl;
A$^1$, A$^2$ and A$^3$ are identical or different and are 1,4-phenylene which may be substituted by one or more groups selected from F, Cl and CN;
M$^1$ and M$^2$ are identical or different and are —CO—O—, —O—CO—, —O—CO—O—, —O—CS—O—, —CH$_2$—O—, —O—CH$_2$—, —CH=CH—, —C—C— or a carbon atoms or an alkoxy group having 1 to 12 carbon atoms; and
m and n are 0 or 1.

7. A process for the preparation of a 2-halo-1,3,4-thiadiazole derivative of the formula (I), as claimed in claim 1

$$X\text{-}B\text{-}A^1\text{-}(M^1\text{-}A^2\text{-})_m(M^2\text{-}A^3)_n\text{-}R^1 \quad (I)$$

in which the symbols and indices are as defined under the formula (I) in claim 1, which comprises
a) reacting 2-amino-1,3,4-thiadiazole with bromine,
b) diazotizing the resultant 2-bromo-1,3,4-thiadiazole using sodium nitrite,
c) reacting the resultant diazonium salt with bromine, and
d) reacting the resultant 2,5-dibromo-1,3,4-thiadiazole with a boron compound of the formula (II)

$$Q^1Q^2\text{-}B\text{-}A^1\text{-}(M^1\text{-}A^2)_m(\text{-}M^2\text{-}A^3)_n\text{-}R^1 \quad (II)$$

in which the symbols and indices are as defined under the formula (I), and
Q$_1$ and Q$_2$ are identical or different and are —OH, C$_1$–C$_4$-alkoxy, C$_1$–C$_4$-alkyl, phenyl, which may be substituted by C$_1$–C$_4$-alkyl, C$_1$–C$_4$-alkoxy or halogen, or halogen or Q$_1$ and Q$_2$ together form a C$_1$–C$_4$-alkylenedioxy group, a methylene group, which may be substituted by one or two C$_1$–C$_4$-alkyl groups, or Q$_1$ and Q$_2$ and the boron atom together are part of a boroxine ring:

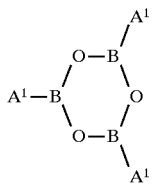

with transition-metal catalysis in an inert solvent at a temperature of from −78° C. to 200° C.

8. The process as claimed in claim 7, wherein the 2-bromo-1,3,4-thiadiazole obtained on bromination of 2-amino-1,3,4-thiadiazole is diazotized in situ.

9. The process as claimed in claim 7, wherein the coupling of 2,5-dibromo-1,3,4,-thiadiazole with a boron compound of the formula (II) is carried out at a temperature of from 30° C. to 170° C.

10. The process as claimed in claim 7, wherein the coupling of 2,5-dibromo-1,3,4-thiadiazole with a boronic acid of the formula (II) is carried out in the presence of a base and in the presence of a phosphine ligand.

* * * * *